(12) United States Patent
Kinoshita et al.

(10) Patent No.: US 10,101,281 B2
(45) Date of Patent: Oct. 16, 2018

(54) SHEET MEMBER CONVEYANCE DEVICE, SHEET MEMBER SUPPORT DEVICE, SHEET MEMBER INSPECTION DEVICE, AND SHEET MEMBER CONVEYANCE METHOD

(71) Applicant: Nippon Electric Glass Co., Ltd., Shiga (JP)

(72) Inventors: Kiyotaka Kinoshita, Shiga (JP); Takayuki Noda, Shiga (JP); Takahide Fujii, Shiga (JP); Masayoshi Yamamoto, Shiga (JP)

(73) Assignee: NIPPON ELECTRIC GLASS CO., LTD., Shiga (JP)

( * ) Notice: Subject to any disclaimer, the term of this patent is extended or adjusted under 35 U.S.C. 154(b) by 0 days.

(21) Appl. No.: 14/906,346

(22) PCT Filed: Jul. 25, 2014

(86) PCT No.: PCT/JP2014/069676
§ 371 (c)(1),
(2) Date: Jan. 20, 2016

(87) PCT Pub. No.: WO2015/019868
PCT Pub. Date: Feb. 12, 2015

(65) Prior Publication Data
US 2016/0178536 A1    Jun. 23, 2016

(30) Foreign Application Priority Data

Aug. 8, 2013 (JP) ................................ 2013-164658

(51) Int. Cl.
*G01N 21/958* (2006.01)
*H01L 21/677* (2006.01)
(Continued)

(52) U.S. Cl.
CPC ......... *G01N 21/958* (2013.01); *B65G 49/066* (2013.01); *B65G 49/067* (2013.01);
(Continued)

(58) Field of Classification Search
CPC . H01L 21/67706; B65H 5/14; B65H 2405/57; G01N 21/958; G01N 21/8914; B65G 49/067; B65G 49/066
(Continued)

(56) References Cited

U.S. PATENT DOCUMENTS 3,290,133 A * 12/1966 Thomas ................. C03B 23/031
65/106
3,341,313 A * 9/1967 Wheeler .................. C03B 35/24
65/104
(Continued)

FOREIGN PATENT DOCUMENTS

CN     1611430     5/2005
CN    101889199    11/2010
(Continued)

OTHER PUBLICATIONS

Hokama et al., Oct. 2009, WO2009118952A1 Translation.*
(Continued)

*Primary Examiner* — Isiaka Akanbi
(74) *Attorney, Agent, or Firm* — Wenderoth, Lind & Ponack, L.L.P.

(57) ABSTRACT

A sheet member conveyance device includes: a support part configured to support a sheet member; and a moving part configured to move the support part to convey the sheet member, the support part including a deformation support part configured to support each of one end portion of the sheet member and another end portion of the sheet member, which are opposed to each other, and to partially deform the sheet member into a curved shape, to thereby form a convex (Continued)

thread portion or a concave thread portion crossing a principal surface of the sheet member.

17 Claims, 6 Drawing Sheets

(51) Int. Cl.
  *B65H 5/14* (2006.01)
  *B65G 49/06* (2006.01)
  *G01N 21/89* (2006.01)
(52) U.S. Cl.
  CPC .......... *B65H 5/14* (2013.01); *G01N 21/8914* (2013.01); *H01L 21/67706* (2013.01); *B65H 2405/57* (2013.01)
(58) Field of Classification Search
  USPC .................................. 356/237.2–237.6, 239.1
  See application file for complete search history.

(56) References Cited

U.S. PATENT DOCUMENTS

| | | | | |
|---|---|---|---|---|
| 4,076,514 A | * | 2/1978 | Kelly | .................... C03B 23/031 65/106 |
| 4,508,556 A | * | 4/1985 | Bennett | .................... C03B 23/03 65/106 |
| 5,071,461 A | * | 12/1991 | Hirotsu | ............. B32B 17/10036 65/104 |
| 5,459,330 A | * | 10/1995 | Venaille | ................ G01N 21/958 250/559.45 |
| 5,691,811 A | * | 11/1997 | Kihira | .................. G01N 21/896 356/239.1 |
| 5,713,976 A | * | 2/1998 | Kuster | ................ C03B 23/0357 65/106 |
| 2015/0014124 A1 | * | 1/2015 | Tagawa | ................... C03B 35/20 198/468.2 |

FOREIGN PATENT DOCUMENTS

| | | | | |
|---|---|---|---|---|
| JP | 2005-172783 | | 6/2005 | |
| JP | 2008-162783 | | 7/2008 | |
| JP | 2009-236771 | | 10/2009 | |
| JP | WO2009118952 A1 | * | 10/2009 | ........... G01N 21/958 |
| WO | 2009/118952 | | 10/2009 | |

OTHER PUBLICATIONS

Office Action dated Aug. 29, 2016 in corresponding Chinese Application No. 201480034577.2, with English translation.
International Search Report dated Oct. 14, 2014 in International (PCT) Application No. PCT/JP2014/069676.
English Translation of the International Preliminary Report on Patentability and Written Opinion of the International Searching Authority dated Feb. 9, 2016 in the International Application No. PCT/JP2014/069676.
Office Action dated Apr. 13, 2017 in corresponding Chinese Application No. 201480034577.2, with partial English translation.

* cited by examiner

SHEET MEMBER CONVEYANCE DEVICE, SHEET MEMBER SUPPORT DEVICE, SHEET MEMBER INSPECTION DEVICE, AND SHEET MEMBER CONVEYANCE METHOD

TECHNICAL FIELD

The present invention relates to a sheet member conveyance device, a sheet member support device, and a sheet member inspection device, which are configured to convey and inspect a sheet member while supporting end portions of the sheet member, and to a sheet member conveyance method.

BACKGROUND ART

As is widely known, in a manufacturing process of glass sheet products typified by a flat panel display, a solar cell, or the like, there has been developed a technology of performing processing and inspection while conveying glass sheets in vertical orientation.

Incidentally, in recent years, there has been an increasing demand for thinner glass sheets in order to reduce weight of the products or the like. For example, thin glass sheets having a sheet thickness of 300 μm or less have been mass-produced. Due to the fact described above, the following problems arise when the glass sheets are conveyed as described above.

Specifically, the glass sheet becomes more liable to be deformed as the glass sheet becomes thinner. Thus, when the thin glass sheet is conveyed in vertical orientation, for example, vibration is liable to occur due to air pressure difference between a front surface side and a back surface side of the glass sheet and a vibration amplitude is liable to be increased. As the vibration described above becomes more significant, the glass sheet becomes more liable to be broken through propagation of microcracks contained in the glass sheet. Further, when the vibration amplitude in the glass sheet is increased during inspection performed through use of an imaging device such as a camera, a region that is displaced in a sheet thickness direction of the glass sheet due to the vibration is liable to be located out of a focal point of the imaging device, thereby sometimes failing to perform accurate inspection of presence or absence of a defect. In view of the above, a technology for solving those problems is disclosed in JP 2009-236771 A.

In JP 2009-236771 A, there is disclosed a sheet member conveyance device including two gripping part groups each including a plurality of gripping parts arrayed away from one another along one of an upper edge portion and a lower edge portion of a glass sheet in vertical orientation, the gripping part groups being configured to grip the upper edge portion and the lower edge portion of the glass sheet to convey the glass sheet along a longitudinal direction of the edge portion, in which the gripping part groups are configured to apply a tensile force between the upper edge portion and the lower edge portion of the glass sheet under a state in which the upper edge portion and the lower edge portion of the glass sheet are gripped.

With the configuration described above, the tensile force can be applied to the glass sheet in the vertical direction during conveyance. Therefore, it is expected that the increase in vibration amplitude may be suppressed owing to the tensile force, and detection accuracy of a defect may be improved when the inspection is performed on the glass sheet through use of the above-mentioned device.

Technical Problem

However, the device disclosed in JP 2009-236771 A still has room for improvement. That is, the tensile force is applied to an entire surface of the glass sheet in the device, and hence, when the glass sheet is curved due to the vibration during conveyance, the tensile stress is applied to the curved region. Therefore, when microcracks are contained in the region, there has been a concern in that the glass sheet is liable to be broken through the propagation of the cracks due to the tensile stress. Further, there has been a problem in that the gripping parts are urged to apply the tensile force to the glass sheet, and hence the gripping parts and the glass sheet are liable to slip on each other so that the glass sheet is liable to slip down and be broken.

SUMMARY OF INVENTION

The present invention has been made in view of the above-mentioned circumstances, and therefore has an object to suppress vibration when a sheet member is supported and conveyed, and to suppress breakage of the sheet member or the like.

Solution to Problem

According to one embodiment of the present invention, which is devised to solve the above-mentioned problems, there is provided a sheet member conveyance device, comprising: a support part configured to support a sheet member; and a moving part configured to move the support part to convey the sheet member, the support part comprising a deformation support part configured to support each of one end portion and another end portion of the sheet member, which are opposed to each other, and to partially deform the sheet member into a curved shape, to thereby form a convex thread portion or a concave thread portion crossing a principal surface of the sheet member.

With the configuration described above, the vibration and the breakage when the sheet member is conveyed can be suppressed. Specifically, the convex thread portion (or concave thread portion) is formed in the sheet member, thereby increasing surface rigidity of the sheet member so that the sheet member is less liable to be deformed. Therefore, the vibration of the sheet member can be suppressed without application of a tensile force or the like. Further, surface oscillation propagated in the sheet member is attenuated or eliminated in the convex thread portion, thereby being capable of suppressing the surface oscillation. When the vibration and the oscillation in the sheet member are suppressed as described above, the breakage of the sheet member can be suppressed.

In the sheet member conveyance device according to the one embodiment of the present invention, it is preferred that the deformation support part comprise a pair of nipping members configured to nip the each of the one end portion and the another end portion of the sheet member, that the pair of nipping members comprise a curved concave portion and a curved convex portion that are fitting to each other, and that the pair of nipping members be configured to nip the sheet member at a gap between the curved concave portion and the curved convex portion to be fitted to each other, to thereby form the convex thread portion or the concave thread portion.

With the configuration described above, the convex thread portion (or concave thread portion) can be easily formed through use of members having a simple configuration. Note that, it is preferred that the pair of nipping members located at the one end portion and the another end portion of the sheet member, which are opposed to each other, be arranged at positions opposed to each other.

In the sheet member conveyance device according to the one embodiment of the present invention, it is preferred that at least one of the curved concave portion or the curved convex portion comprise an elastic member.

With the configuration described above, when the sheet member is nipped by the nipping members, the nipping members are elastically deformed, thereby being capable of preventing local deformation of the sheet member. With this, the breakage of the sheet member can be prevented.

In the sheet member conveyance device according to the one embodiment of the present invention, it is preferred that the deformation support part comprise a plurality of deformation support parts configured to form a plurality of convex thread portions or a plurality of concave thread portions in the sheet member in parallel to one another.

With the configuration described above, bending rigidity of the sheet member can be further increased, thereby being capable of effectively suppressing the vibration of the sheet member.

It is preferred that the sheet member conveyance device according to the one embodiment of the present invention further comprise a plurality of flattening support parts configured to nip and support end portions of the sheet member without deforming the sheet member.

With the configuration described above, flat portions of the sheet member can be supported, thereby enabling stable support and conveyance.

In the sheet member conveyance device according to the one embodiment of the present invention, it is preferred that the sheet member comprise a rectangular glass sheet having a thickness of 1 mm or less, that the deformation support part be configured to support each of an upper end edge portion and a lower end edge portion of the sheet member so that the sheet member is held in upright orientation, and that the moving part be configured to move the deformation support part in a principal surface direction of the sheet member.

With the configuration described above, the sheet member having a small thickness and being liable to be vibrated with a large amplitude during the conveyance can be stably supported and conveyed in vertical orientation.

According to one embodiment of the present invention, there is provided a sheet member inspection device, comprising a defect inspection part, which is arranged in a conveyance path of the sheet member conveyed by the above-mentioned sheet member conveyance device, and is configured to inspect presence or absence of a defect contained in the sheet member.

According to one embodiment of the present invention, there is provided a sheet member support device, comprising a deformation support part configured to nip each of one edge portion and another edge portion of a sheet member, which are opposed to each other, and to partially deform the sheet member into a curved shape, to thereby form a convex thread portion or a concave thread portion extending over a region from the one edge portion to the another edge portion.

According to one embodiment of the present invention, there is provided a sheet member conveyance method, comprising the steps of: supporting each of one end portion and another end portion of a sheet member, which are opposed to each other, and partially deforming the sheet member into a curved shape, to thereby form a convex thread portion or a concave thread portion extending over a region from the one edge portion to the another edge portion; and conveying the sheet member under a state in which the convex thread portion or the concave thread portion is formed.

Further, according to one embodiment of the present invention, which is devised to solve the above-mentioned problems, there is provided a sheet member conveyance device, comprising two support part groups each comprising a plurality of support parts arrayed away from one another along one of a pair of opposed edge portions of a sheet member in vertical orientation, the two support part groups being configured to support the pair of opposed edge portions of the sheet member to convey the sheet member along a longitudinal direction of the pair of opposed edge portions, wherein the two support part groups are configured to apply a tensile force between the pair of opposed edge portions of the sheet member under a state in which the pair of opposed edge portions of the sheet member are supported, and wherein each of the two support part groups is configured to apply another tensile force at least between one of the plurality of support parts in a state of supporting one end portion of the one of the pair of opposed edge portions of the sheet member and another one of the plurality of support parts in a state of supporting another end portion of the one of the pair of opposed edge portions of the sheet member.

When the two support part groups apply the tensile force (hereinafter referred to as "first-direction tensile force" (N)) between the pair of edge portions of the sheet member under a state in which the pair of edge portions of the sheet member are supported, the vibration amplitude at a front end portion and a rear end portion of the sheet member in a conveyance direction of the sheet member can be reduced. Further, under the above-mentioned state, when each of the support part groups applies a tensile force (hereinafter referred to as "second-direction tensile force" (N)) at least between one of the plurality of support parts in a state of supporting the one end portion of the one edge portion of the sheet member and another one of the plurality of support parts in a state of supporting the another end portion of the one edge portion of the sheet member, the vibration amplitude at a center portion can also be reduced. Based on the above-mentioned configuration, when the second-direction tensile force is applied to the sheet member under a state in which the first-direction tensile force is applied to the sheet member, a maximum value of displacement of the sheet member in a sheet thickness direction of the sheet member due to the vibration can be reduced to the extent possible. That is, the vibration amplitude in the entire sheet member can be reduced. As a result, the breakage of the sheet member or the like can be suppressed. Note that, when both of the first-direction tensile force and the second-direction tensile force are applied as described above, the vibration amplitude at the front end portion and the rear end portion is increased as compared to a case where only the first-direction tensile force is applied. Further, as the second-direction tensile force is increased, the vibration amplitude at the center portion is gradually reduced, whereas the vibration amplitude at the front end portion and the rear end portion is gradually increased.

In the sheet member conveyance device according to the one embodiment of the present invention, it is preferred that positions to be supported by the plurality of support parts of the each of the two support part groups be symmetrical with respect to a center portion of the one of the pair of opposed edge portions, and that the plurality of support parts of one of the two support part groups and the plurality of support parts of another one of the two support part groups be configured to support the same positions in the longitudinal direction of the pair of opposed edge portions.

With the configuration described above, the positions to be supported by the support parts of the one of the support part groups and the support parts of the another one of the support part groups are arranged point symmetrical with respect to a center of a surface of the sheet member. With this, the first-direction tensile force and the second-direction tensile force can be applied to the entire sheet member in a well-balanced manner, thereby being capable of enhancing the effect of reducing the vibration amplitude.

In the sheet member conveyance device according to the one embodiment of the present invention, it is preferred that the each of the two support part groups be configured to apply the another tensile force between all of the plurality of support parts, which are adjacent to each other, with respect to the center portion of the one of the pair of opposed edge portions.

With the configuration described above, the second-direction tensile force can be applied to an entire region of the sheet member from the front end portion to the rear end portion in the conveyance direction. Due to the above, the effect of reducing the vibration amplitude in the entire sheet member can be further enhanced.

In the sheet member conveyance device according to the one embodiment of the present invention, it is preferred that a magnitude of the tensile force to be applied to the sheet member by the plurality of support parts be configured to be adjusted by an air pressure or a hydraulic pressure.

With the configuration described above, the magnitude of each of the first-direction tensile force and the second-direction tensile force to be applied to the sheet member can be easily adjusted depending on a magnitude of the pressure.

According to one embodiment of the present invention, there is provided a sheet member inspection device, comprising a defect inspection part, which is arranged in a conveyance path of the sheet member conveyed by the sheet member conveyance device, and is configured to inspect presence or absence of a defect contained in the sheet member.

In the sheet member inspection device according to the one embodiment of the present invention, it is preferred that the defect inspection part be configured to scan and inspect an effective surface of the sheet member, and that the each of the two support part groups be configured to vary, depending on an inspection region of the sheet member, the magnitude of the tensile force to be applied between the plurality of support parts adjacent to each other along the one of the pair of opposed edge portions.

With the configuration described above, when the magnitude of the second-direction tensile force to be applied between the adjacent support parts is varied, a magnitude of the vibration amplitude at the front end portion and the rear end portion of the sheet member in the conveyance direction and a magnitude of the vibration amplitude at the center portion of the sheet member in the conveyance direction can be controlled. Therefore, when the vibration amplitude in the inspection region is controlled to be reduced along with the shift of the inspection region, the presence or absence of a defect can be inspected with high accuracy.

In the sheet member inspection device according to the one embodiment of the present invention, it is preferred that the defect inspection part be configured to inspect an entire region of the effective surface of the sheet member while causing the sheet member to be conveyed.

With the configuration described above, the vibration amplitude of the entire sheet member, which is conveyed by the sheet member conveyance device, is reduced, and hence the presence or absence of a defect in the entire region of the effective surface of the sheet member can be inspected with high accuracy.

In the sheet member inspection device according to the one embodiment of the present invention, it is preferred that, when inspection is performed on a region from a front end portion of the sheet member in a conveyance direction of the sheet member to a center portion of the sheet member in the conveyance direction, the each of the two support part groups gradually increases the another tensile force to be applied between the plurality of support parts adjacent to each other along the one of the pair of opposed edge portions as the inspection region is shifted from the front end portion in the conveyance direction to the center portion in the conveyance direction, and that, when inspection is performed on a region from the center portion of the sheet member in the conveyance direction to a rear end portion of the sheet member in the conveyance direction, the each of the two support part groups gradually reduce the another tensile force to be applied between the plurality of support parts adjacent to each other along the one of the pair of opposed edge portions as the inspection region is shifted from the center portion in the conveyance direction to the rear end portion in the conveyance direction.

With the configuration described above, when the inspection is performed on the front end portion and the rear end portion of the sheet member in the conveyance direction, influence of the first-direction tensile force to be applied to the sheet member becomes larger, thereby being capable of reducing the vibration amplitude at the front end portion and the rear end portion. On the other hand, when the inspection is performed on the center portion, both of the first-direction tensile force and the second-direction tensile force are applied to the sheet member, thereby being capable of reducing the vibration amplitude at the center portion. Based on the above-mentioned configuration, in the entire region of the effective surface of the sheet member, the presence or absence of a defect can be inspected with higher accuracy. In this case, when the inspection is performed on the front end portion and the rear end portion, it is preferred that the second-direction tensile force be zero and only the first-direction tensile force be applied to the sheet member. Further, when the inspection is performed on the center portion, it is preferred that the second-direction tensile force be increased to the extent possible within a range in which inconvenience such as breakage is not caused in the sheet member. In this manner, in each region, the vibration amplitude can be further reduced and even more accurate inspection can be performed.

According to one embodiment of the present invention, there is provided a sheet member conveyance method, comprising: supporting a pair of opposed edge portions of a sheet member in vertical orientation by two support part groups each comprising a plurality of support parts arrayed away from one another along one of the pair of opposed edge portions; conveying the sheet member along a longitudinal direction of the pair of opposed edge portions; applying, during the conveying of the sheet member, by the two support part groups, a tensile force between the pair of opposed edge portions of the sheet member under a state in which the pair of opposed edge portions of the sheet member are supported; and applying, by each of the two support part groups, another tensile force at least between one of the plurality of support parts in a state of supporting one end portion of the one of the pair of opposed edge portions of the sheet member and another one of the plurality of support parts in a state of supporting another end portion of the one of the pair of opposed edge portions of the sheet member.

Advantageous Effects of Invention

As described above, according to the one embodiment of the present invention, the vibration amplitude in the sheet member can be reduced when the sheet member is conveyed in vertical orientation.

DESCRIPTION OF EMBODIMENTS

Now, description is given of embodiments of the present invention referring to the attached drawings.

First Embodiment

Figure 1:
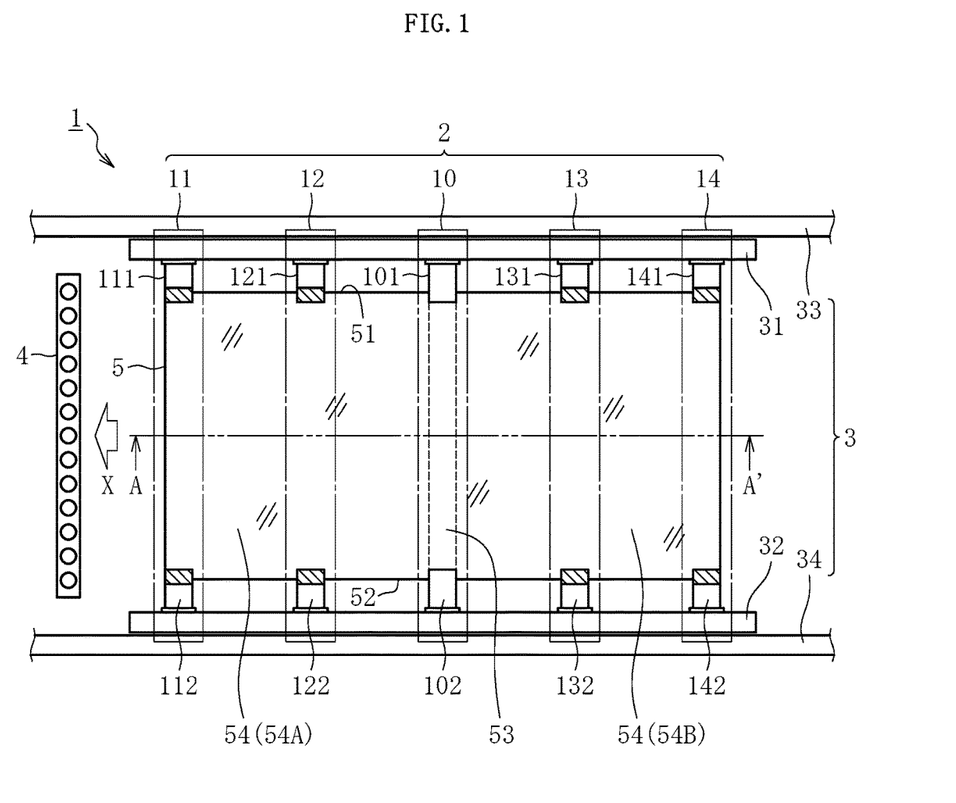
FIG. 1 is a front view for illustrating a sheet member conveyance device, a sheet member support device, and a sheet member inspection device according to a first embodiment of the present invention.
Figure 2:
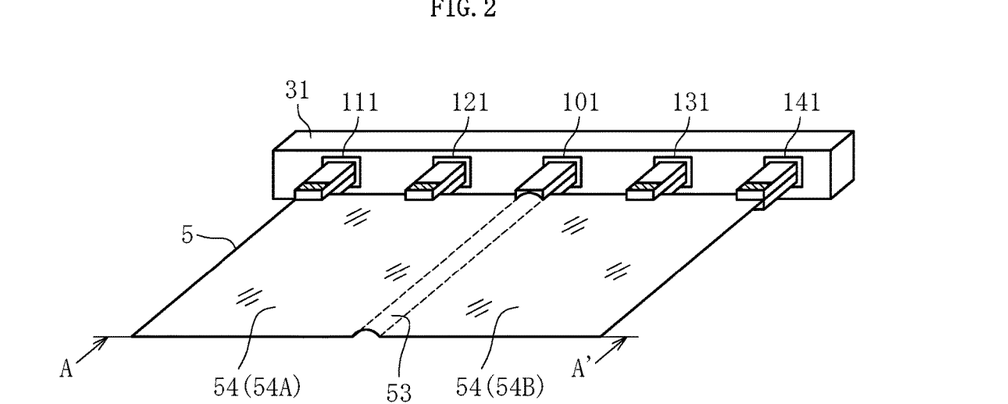
FIG. 2 is a sectional perspective view of a part taken along the line AA' of FIG. 1, for illustrating the sheet member conveyance device, the sheet member support device, and the sheet member inspection device according to the first embodiment of the present invention.

FIG. 1 is a view for illustrating a sheet member conveyance device 1, a sheet member support device 2, and a sheet member inspection device according to a first embodiment of the present invention. Further, FIG. 2 is a sectional perspective view taken along the line AA' of FIG. 1.

The sheet member conveyance device 1 comprises the sheet member support device 2 serving as a support part that is configured to support a sheet member, and a moving mechanism 3 serving as a moving part that is configured to move the sheet member support device 2. Further, the sheet member inspection device comprises the sheet member conveyance device 1 and a line sensor 4. The line sensor 4 serving as a defect inspection part, which is arranged in a conveyance path of the sheet member, inspects presence or absence of a defect contained in the sheet member conveyed by the sheet member conveyance device 1 in vertical orientation in a conveyance direction X (horizontal direction). Note that, in the first embodiment of the present invention and a second embodiment of the present invention to be described later, description is given taking an example of a case where a glass sheet 5 serving as the sheet member is to be supported, conveyed, and inspected.

The sheet member support device 2 comprises chuck pairs 10 to 14 configured to support each of an upper edge portion 51 and a lower edge portion 52 of the glass sheet 5 in vertical orientation. More specifically, the sheet member support device 2 comprises the chuck pair 10 serving as a deformation support part that is configured to support (nip) the glass sheet 5 while partially deforming the glass sheet 5 into a curved shape, and the chuck pairs 11 to 14 serving as flattening support parts that are configured to support (nip) the glass sheet 5 into a flat shape without deforming the glass sheet 5. The glass sheet 5 supported by the sheet member support device 2 is divided into a convex thread portion 53 corresponding to a partially curved region (concave thread portion when viewed from a back side) and flat portions 54 corresponding to other flat regions.

The moving mechanism 3 comprises an upper frame 31, a lower frame 32, an upper guide rail 33, and a lower guide rail 34. The upper frame 31 and the lower frame 32 are each a plate-like bar member having the chuck pairs 10 to 14 fixed thereto. The upper frame 31 and the lower frame 32 are configured to be movable respectively along the upper guide rail 33 and the lower guide rail 34. A drive source of the upper frame 31 and the lower frame 32 is, for example, a widely-known drive source such as a servo motor. It is preferred that a width dimension of each of the upper frame 31 and the lower frame 32 be determined depending on a width dimension of the glass sheet 5, and that a separation distance between the upper frame 31 and the lower frame 32 be determined depending on a length dimension of the glass sheet 5.

A more specific description is given herein. The chuck pair 10 comprises deformation support chucks 101 and 102, the chuck pair 11 comprises flattening support chucks 111 and 112, the chuck pair 12 comprises flattening support chucks 121 and 122, the chuck pair 13 comprises flattening support chucks 131 and 132, and the chuck pair 14 comprises flattening support chucks 141 and 142. The deformation support chuck 101 and the flattening support chucks 111, 121, 131, and 141 are arranged to be fixed to the upper frame 31 with predetermined intervals secured therebetween. Further, the deformation support chuck 102 and the flattening support chucks 112, 122, 132, and 142 are arranged to be fixed to the lower frame 32 with predetermined intervals secured therebetween. In this way, the support chucks in pairs are arranged so as to be opposed to each other in the vertical direction.

The deformation support chuck 101 and the flattening support chucks 111, 121, 131, and 141 nip the upper edge portion 51 of the glass sheet 5, whereas the deformation support chuck 102 and the flattening support chucks 112, 122, 132, and 142 nip the lower edge portion 52 of the glass sheet 5. At this time, the respective support chucks support positions opposed in a direction along each of the upper edge portion 51 and the lower edge portion 52. Under a state in which the glass sheet 5 is supported as described above, the upper frame 31 is moved along the upper guide rail 33 and the lower frame 32 is moved along the lower guide rail 34. With this, the glass sheet 5 is moved in vertical orientation in a principal surface direction (direction X illustrated in FIG. 1).

Note that, the positions at which the respective support chucks support the glass sheet 5 may be determined arbitrarily. However, it is preferred that the positions be point symmetrical with respect to a center of the principal surface of the glass sheet 5. That is, the flattening support chuck 111 and the flattening support chuck 142, and the flattening support chuck 122 and the flattening support chuck 131 are respectively located at positions point symmetrical with respect to the center of the principal surface of the glass sheet 5. The flattening support chuck 111 is opposed to the flattening support chuck 112, and the flattening support chuck 142 is opposed to the flattening support chuck 141, respectively. Further, it is preferred that any one of the support chucks support a front end portion and a rear end portion of each of the upper edge portion 51 and the lower edge portion 52 in the conveyance direction X. With the configuration described above, the glass sheet 5 can be supported and conveyed more stably.

In the glass sheet 5 nipped by the deformation support chucks 101 and 102, the convex thread portion 53, which crosses the principal surface of the glass sheet 5, is formed over a region from a portion nipped by the deformation support chuck 101 to a portion nipped by the deformation support chuck 102. Now, the configuration of the deformation support chucks is described with reference to FIG. 3 and FIGS. 4(a) and 4(b). Note that, the deformation support chucks 101 and 102 have the same configuration, and hence the configuration of the deformation support chuck 101 is described below as a representative example.

Figure 3:
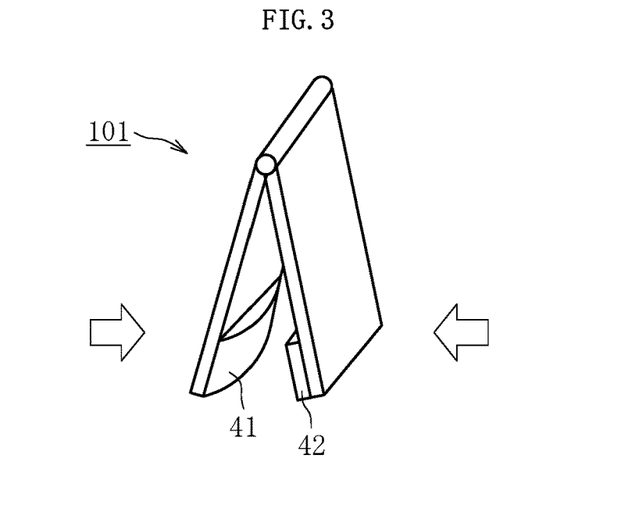
FIG. 3 is a view for illustrating a structure of a deformation support chuck.

FIG. 3 is a schematic view for illustrating the configuration of the deformation support chuck 101. As illustrated in FIG. 3, the deformation support chuck 101 comprises a curved convex portion 41 and a curved concave portion 42 that are fitting to each other. The curved convex portion 41 has a columnar fitting surface. The curved shape of the fitting surface may be an ellipse or a complete circle.

Figure 4A:
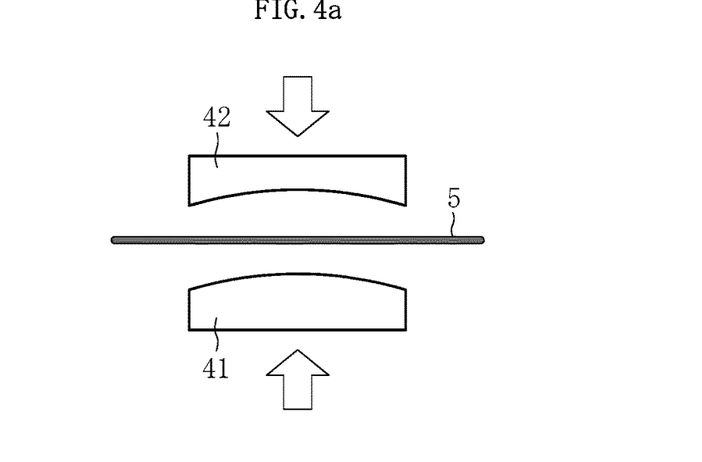
FIG. 4a is a view for illustrating how the deformation support chuck deforms a glass sheet.
Figure 4B:
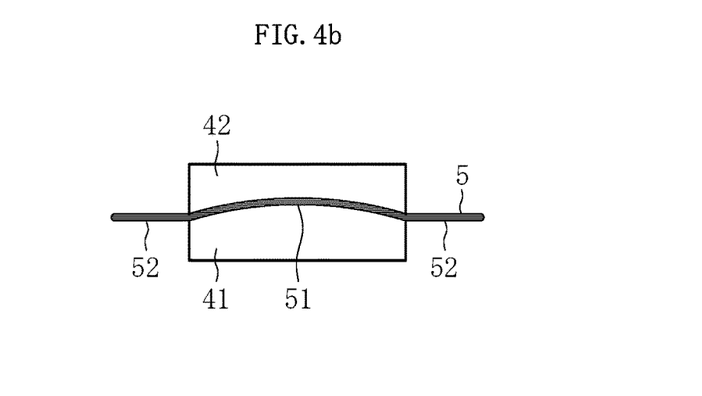
FIG. 4b is a view for illustrating how the deformation support chuck deforms the glass sheet.

FIGS. 4(a) and 4(b) are views for illustrating how the glass sheet 5 is deformed by the deformation support chuck 101. The curved convex portion 41 and the curved concave portion 42 are opened and closed through movement in a sheet thickness direction of the glass sheet 5. With this, the upper edge portion 51 or the lower edge portion 52 of the glass sheet 5 is supported and the support thereof is released. Under a state in which the deformation support chuck 101 is opened, the glass sheet 5 is arranged between the curved convex portion 41 and the curved concave portion 42 (FIG. 4(a)), and then the curved convex portion 41 and the curved concave portion 42 are close to be fitted to each other (FIG. 4(b)). With this, the convex thread portion 53 is formed in the glass sheet 5. An opening/closing mechanism for the deformation support chuck 101 is, for example, a widely-known mechanism such as an air cylinder.

Note that, it is preferred that a region of at least one of the curved convex portion 41 or the curved concave portion 42 to be brought into abutment against the glass sheet 5 be, for example, formed of a material having high elasticity, such as rubber. Similarly, it is preferred that a region of the respective flattening support chucks to be brought into abutment against the glass sheet 5 be also formed of an elastic member. With the configuration described above, when the glass sheet 5 is nipped, an excessive stress is prevented from being applied to a nip portion of the glass sheet 5, thereby being capable of preventing breakage of the glass sheet 5.

As illustrated in FIG. 1, the line sensor 4 is arranged in a conveyance path of the glass sheet 5 and detects a defect contained in the glass sheet 5. The line sensor 4 comprises a plurality of image pickup elements such as CCDs along the vertical direction. Further, the image pickup elements of the line sensor 4 receive light, which is radiated from a light source (not shown) set on an opposite side across the glass sheet 5 toward the surface of the glass sheet 5 during conveyance passing in front of the line sensor 4 and is transmitted through the glass sheet 5. The light source is, for example, an LED line light source provided along the line sensor 4. The image pickup elements of the line sensor 4 inspect (scan) the presence or absence of a defect contained in the glass sheet 5 based on change in light intensity of the received light. Defects to be detected are, for example, bubbles and stones in the inside of or on the surface of the glass sheet 5. Note that, the inspection (scanning) is gradually performed on the entire region of the glass sheet 5 from the front end portion to the rear end portion in the conveyance direction X.

Note that, a method of inspecting the presence or absence of a defect in the glass sheet 5 is not limited to the method described above. For example, both of the light source and the line sensor 4 may be arranged on one principal surface side of the glass sheet 5 so that the line sensor 4 receives light reflected by the glass sheet 5, thereby detecting a defect in the glass sheet 5. Further, the light source may be a point light source, which performs scanning along a light receiving portion of the line sensor 4. Note that, for example, an LED, a metal halide lamp, or a laser light source may be used as the light source.

As described above, in the sheet member conveyance device 1 according to the first embodiment of the present invention, the convex thread portion 53 is formed in the glass sheet 5, and hence bending rigidity of the glass sheet 5 is higher as compared to the case where no convex thread portion 53 is formed. With this, the glass sheet 5 is less liable to be deformed. As a result, a vibration amplitude in the glass sheet 5 in the sheet thickness direction can be reduced. Therefore, the breakage of the glass sheet 5 due to the vibration is more easily prevented. Further, surface oscillation propagated in the sheet member is attenuated or eliminated in the convex thread portion 53, thereby being capable of suppressing the surface oscillation. For example, the oscillation occurring in the flat portion 54A on the front end side is attenuated or eliminated in the convex thread portion 53, and hence is less liable to be propagated to the flat portion 54B on the rear end side. When the vibration and the surface oscillation in the sheet member are suppressed as described above, for example, cracks can be prevented from being propagated and the breakage can be suppressed in a case where the sheet member is formed of glass. Further, when a defect is to be inspected by the line sensor 4, the glass sheet 5 is easily prevented from being vibrated to be located out of a focal point of the line sensor 4. That is, the presence or absence of a defect in the glass sheet 5 can be inspected with high accuracy.

Second Embodiment

Figure 5:
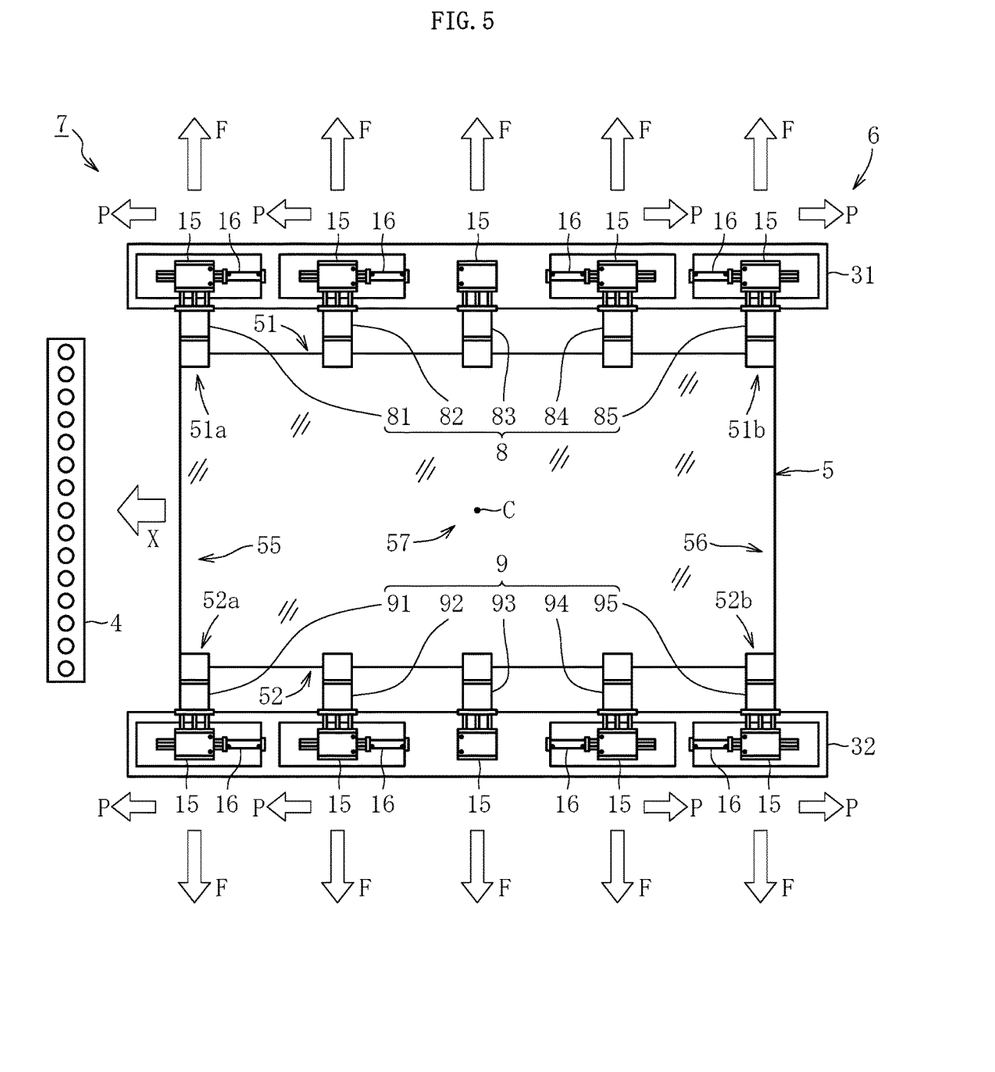
FIG. 5 is a front view for illustrating a sheet member conveyance device and a sheet member inspection device according to a second embodiment of the present invention.

FIG. 5 is a front view for illustrating a sheet member conveyance device 6 and a sheet member inspection device 7 according to a second embodiment of the present invention. Note that, in the description of the second embodiment, components already described in the first embodiment described above are denoted by the same reference symbols in the figures referred to in the description of the second embodiment, to thereby omit redundant description.

As illustrated in FIG. 5, the sheet member inspection device 7 is configured such that the line sensor 4 serving as a defect inspection part, which is arranged in a conveyance path of the glass sheet 5, inspects presence or absence of a defect contained in the glass sheet 5 conveyed by the sheet member conveyance device 6 in vertical orientation in the conveyance direction X (horizontal direction).

The sheet member conveyance device 6 comprises two chuck groups 8 and 9 each serving as a support part group, which is configured to support (grip) the upper edge portion 51 and the lower edge portion 52 being a pair of vertically-opposed edge portions of the glass sheet 5 in vertical orientation. The chuck groups 8 and 9 respectively comprise five chucks 81 to 85 and five chucks 91 to 95 each serving as a plurality of support parts arrayed away from one another along the upper edge portion 51 and the lower edge portion 52. Further, the chuck groups 8 and 9 each comprising the five chucks as one group support symmetrical positions with respect to a center portion of the upper edge portion 51 and a center portion of the lower edge portion 52. Further, the chucks of the chuck group 8 and the chucks of the chuck group 9 respectively support positions opposed in the vertical direction (the same positions on the upper edge portion 51 and the lower edge portion 52 in a longitudinal direction). With the configuration described above, the positions to be supported by the respective chucks of both the chuck groups 8 and 9 are point symmetrical with respect to a center C of the surface of the glass sheet 5. In addition, of the chucks, the chucks 81 and 91 respectively support front end portions 51a and 52a of the upper edge portion 51 and the lower edge portion 52 in the conveyance direction X, whereas the chucks 85 and 95 respectively support rear end portions 51b and 52b of the upper edge portion 51 and the lower edge portion 52 in the conveyance direction X.

Further, in the respective chucks, support portions each configured to support the upper edge portion 51 or the lower edge portion 52 is formed of a pair of flat plate-like members extending along the surface of the glass sheet 5 in the vertical direction. The support portions are opened and closed through movement in the sheet thickness direction. With this, the upper edge portion 51 or the lower edge portion 52 is supported (gripped) and the support thereof is released. In addition, in the flat plate-like member, an abutment portion to be directly brought into abutment against the upper edge portion 51 or the lower edge portion 52 is formed of, for example, a material having high elasticity, such as rubber.

Further, each chuck is coupled to a piston enclosed in a first air cylinder 15. Compressed air can be sent from an air supply device (such as an air compressor) (not shown) into the first air cylinder 15. Further, the air inside the first air cylinder 15 can be sucked by an air suction device (such as a vacuum pump) (not shown) to be exhausted. Further, an air pressure inside the cylinder is adjusted by the air supply device and the air suction device so that the piston enclosed in the cylinder is moved due to the pressure. With this, each chuck is moved in the vertical direction. Along with the movement of each chuck, a tensile force F (hereinafter referred to as "first-direction tensile force F") is applied to the glass sheet 5 in the vertical direction. In this case, the magnitude of the first-direction tensile force F to be applied from each chuck to the glass sheet 5 is the same, and may be set arbitrarily within a range capable of supporting (gripping) the glass sheet 5. For example, it is preferred that the magnitude of the first-direction tensile force F be set such that the tensile force per unit supporting area (unit gripping area) is from 5 $kN/m^2$ to 500 $kN/m^2$ for one chuck. Note that, when the tensile force per unit supporting area is 5 $kN/m^2$ or less for each chuck, an effect of reducing the vibration amplitude is difficult to be obtained. Further, when the tensile force per unit supporting area is 500 $kN/m^2$ or more for each chuck, the glass sheet 5 is more liable to slip off the chuck, thereby being difficult to support the glass sheet 5 stably.

In addition, except for the first air cylinders 15 enclosing the pistons coupled to the chucks 83 and 93, all the other first air cylinders 15 are coupled to pistons enclosed in second air cylinders 16. Similarly to the first air cylinder 15, an air pressure inside the second air cylinder 16 is adjusted by an air supply device (not shown) and an air suction device (not shown). Further, the piston enclosed in the cylinder is moved due to change in the air pressure. With this, each chuck is moved in the horizontal direction. Along with the movement of each chuck, a tensile force P (hereinafter referred to as "second-direction tensile force P") is applied to an entire region of the glass sheet 5 from a front end portion 55 to a rear end portion 56 in the conveyance direction T. In this case, the magnitude of the second-direction tensile force P to be applied from each chuck to the glass sheet 5 is the same, and may be set arbitrarily within a range capable of supporting (gripping) the glass sheet 5. For example, it is preferred that the magnitude of the second-direction tensile force P be set such that the tensile force per unit supporting area (unit gripping area) is from 3 $kN/m^2$ to 300 $kN/m^2$ for one chuck.

Further, the second air cylinders 15 are respectively fixed to the frames 31 and 32. Note that, the first air cylinders 15 enclosing the pistons coupled to the chucks 83 and 93 are respectively fixed to the frames 31 and 32 directly.

Now, actions and effects, which are to be obtained when the presence or absence of a defect contained in the glass sheet 5 is inspected while conveying the glass sheet 5 in vertical orientation through use of the above-mentioned sheet member conveyance device 6 and the above-mentioned sheet member inspection device 7, are described with reference to the attached drawings.

When the first-direction tensile force F is applied to the glass sheet 5 during conveyance, the vibration amplitude at each of the front end portion 55 and the rear end portion 56 of the glass sheet 5 in the conveyance direction X is reduced. However, the vibration amplitude at the center portion 57 remains large. That is, under this state, displacement of the glass sheet 5 in the sheet thickness direction due to the vibration is at the maximum at the center portion 57.

Figure 6:
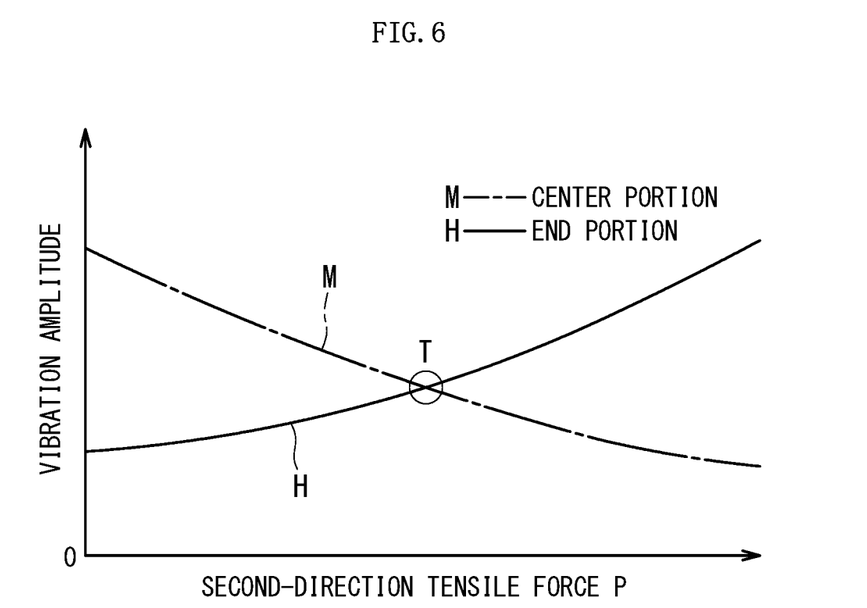
FIG. 6 is a graph for showing a relationship between a second-direction tensile force applied to a glass sheet and an amplitude of vibration occurring in the glass sheet.

The inventors of the present invention have reached the following findings as a result of diligent research. When the second-direction tensile force P is applied to the glass sheet 5 while maintaining a constant magnitude of the first-direction tensile force F under the above-mentioned state, a vibration amplitude M at the center portion 57 is gradually reduced along with increase in the second-direction tensile force P as shown in FIG. 6. Further, as shown in FIG. 6, a vibration amplitude H at each of the front end portion 55 and the rear end portion 56 (in FIG. 6, the front end portion 55 and the rear end portion 56 are collectively referred to as "end portion") are gradually increased along with the increase in the second-direction tensile force P contrary to the center portion 57. The amplitude H eventually surpasses the vibration amplitude M at the center portion 57, and the displacement of the glass sheet 5 in the sheet thickness direction due to the vibration is at the maximum at the front end portion 55 or the rear end portion 56.

Based on such findings, the magnitude of the second-direction tensile force P is adjusted while maintaining the constant magnitude of the first-direction tensile force F to be applied to the glass sheet 5 so that the vibration amplitude M at the center portion 57 and the vibration amplitude H at each of the front end portion 55 and the rear end portion 56 are substantially the same as each other as in a circled point T in FIG. 6. With this, a maximum value of the displacement of the glass sheet 5 in the sheet thickness direction due to the vibration can be reduced to the extent possible. That is, the vibration amplitude in the entire glass sheet 5 can be reduced. As a result, the breakage of the glass sheet 5 or the like can be suppressed.

Further, in the above-mentioned sheet member conveyance device 6, the positions to be supported by the respective chucks are arranged so as to be point symmetrical with respect to the center C of the surface of the glass sheet 5, and hence the first-direction tensile force F and the second-direction tensile force P can be applied to the entire glass sheet 5 in a well-balanced manner. Further, the second-direction tensile force P can be applied to the entire region of the glass sheet 5 from the front end portion 55 to the rear end portion 56 in the conveyance direction X. Due to the above, the effect of reducing the vibration amplitude in the entire glass sheet 5 can be further enhanced. In addition, the air pressure of the air inside the first air cylinder 15 and the second air cylinders 16 is controlled, thereby being capable of easily adjusting the magnitude of each of the first-direction tensile force F and the second-direction tensile force P to be applied to the glass sheet 5.

As a result of the above-mentioned matters, in the entire glass sheet 5 conveyed by the sheet member conveyance device 6, the vibration amplitude is reduced, and hence the presence or absence of a defect in the entire region of an effective surface of the glass sheet 5 can be inspected by the sheet member inspection device 7 with high accuracy.

Further, when the magnitude of the second-direction tensile force P to be applied to the glass sheet 5 is changed in a mode as described below along with a shift of an inspection region from the front end portion 55 toward the rear end portion 56 of the glass sheet 5 in the conveyance direction X, a defect can be inspected with higher accuracy.

Figure 7:
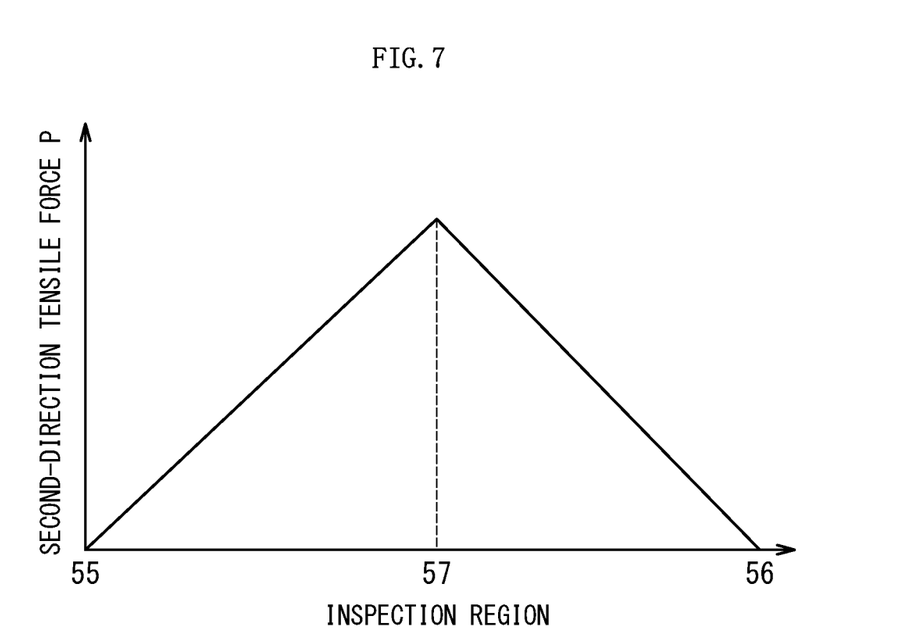
FIG. 7 is a graph for showing a relationship between an inspection region of the glass sheet and the second-direction tensile force applied to the glass sheet.

That is, as shown in FIG. 7, when the inspection is performed on the glass sheet 5 from the front end portion 55 to the center portion 57 in the conveyance direction X, the second-direction tensile force P is gradually increased from zero as the inspection region is shifted from the front end portion 55 to the center portion 57. Further, when the inspection is performed from the center portion 57 to the rear end portion 56, the second-direction tensile force P is gradually reduced to zero as the inspection region is shifted from the center portion 57 to the rear end portion 56.

Figure 8A:
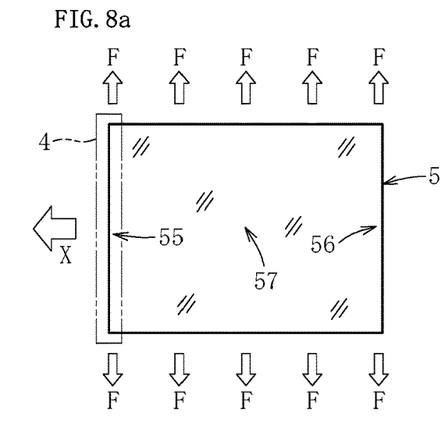
FIG. 8a is a front view for illustrating how a defect in the glass sheet is inspected through use of the sheet member inspection device according to the second embodiment of the present invention.

In this manner, as illustrated in FIG. 8a (components other than the glass sheet 5 are not shown), when the inspection is performed on the front end portion 55 of the glass sheet 5 in the conveyance direction X, only the first-direction tensile force F is applied to the glass sheet 5, thereby being capable of reducing the vibration amplitude at the front end portion 55 to the extent possible.

Figure 8B:
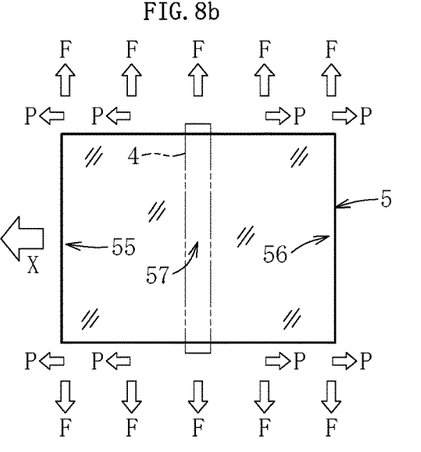
FIG. 8b is a front view for illustrating how a defect in the glass sheet is inspected through used of the sheet member inspection device according to the second embodiment of the present invention.

Further, as illustrated in FIG. 8b (components other than the glass sheet 5 are not shown), when the inspection region is shifted from the front end portion 55 to the center portion 57, both of the first-direction tensile force F and the second-direction tensile force P are applied to the glass sheet 5, and the second-direction tensile force P is at the maximum when inspection is performed on the center portion 57. With this, the vibration amplitude at the center portion 57 can be reduced to the extent possible.

Figure 8C:
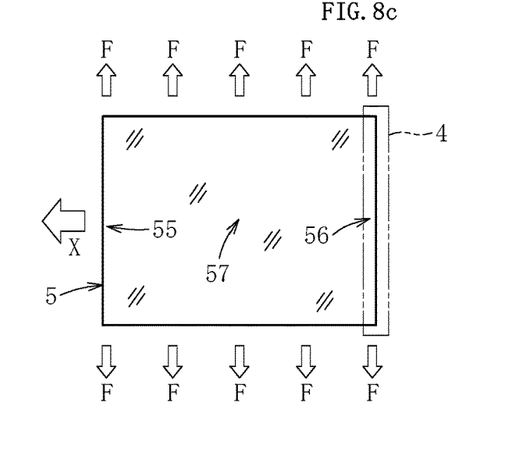
FIG. 8c is a front view for illustrating how a defect in the glass sheet is inspected through use of the sheet member inspection device according to the second embodiment of the present invention.

Further, as illustrated in FIG. 8c (components other than the glass sheet 5 are not shown), when the inspection region is shifted to the rear end portion 56, similarly to the inspection of the front end portion 55, only the first-direction tensile force F is applied to the glass sheet 5, thereby being capable of reducing the vibration amplitude at the rear end portion 56 to the extent possible.

As described above, the magnitude of the second-direction tensile stress P is controlled depending on the inspection region, thereby enabling further accurate inspection of presence or absence of a defect in the entire region of the effective surface of the glass sheet 5. Note that, as the second-direction tensile force P is increased, the vibration amplitude at the center portion 57 is reduced. Thus, when the inspection is performed on the center portion 57 in this mode, it is preferred that the second-direction tensile force P be increased to the extent possible within a range in which inconvenience such as breakage is not caused in the glass sheet 5. Further, when inspection is performed on the front end portion 55 and the rear end portion 56, the magnitude of the second-direction tensile force P need not necessarily be zero. However, in order to reduce the vibration amplitude at each of the front end portion 55 and the rear end portion 56 to the extent possible, it is preferred that the magnitude of the second-direction tensile force P be zero or substantially zero.

In this case, the configurations of the sheet member conveyance device and the sheet member inspection device according to the present invention are not limited to the configurations of the above-mentioned respective embodiments. In the above-mentioned first embodiment, the upper edge portion and the lower edge portion are supported by the five pairs of chucks, but the numbers of the chucks and support portions may be changed arbitrarily as long as the upper edge portion and the lower edge portion are supported by a plurality of chucks comprising at least one pair of deformation support chucks. For example, a plurality of pairs of deformation support chucks may be provided so that a plurality of convex thread portions are formed in the glass sheet in parallel to one another. With this, the bending rigidity of the glass sheet can be enhanced to effectively suppress the vibration of the glass sheet.

Further, in the above-mentioned second embodiment, each of the upper edge portion and the lower edge portion is supported by the five chucks. However, at least the chuck configured to support the front end portion of each of the upper edge portion and the lower edge portion in the conveyance direction and the chuck configured to support the rear end portion of each of the upper edge portion and the lower edge portion in the conveyance direction only need to be provided. Further, the number of the chucks configured to support the upper edge portion and the number of the chucks configured to support the lower edge portion may be different from each other.

Further, in the above-mentioned respective embodiments, the respective chucks support the positions point symmetrical with respect to the center point of the surface of the glass sheet. However, arrangement of the respective chucks may not be limited to the arrangement described above.

Further, in the above-mentioned second embodiment, the first air cylinders are provided on both of the upper edge portion side and the lower edge portion side, and the first-direction tensile force is applied to the glass sheet through the movement of the chucks coupled to the pistons enclosed in the first air cylinders. However, the first air cylinder may be provided on only one of the upper edge portion side and the lower edge portion side. For example, in a case where the first air cylinder is provided only on the upper edge portion side, when the first-direction tensile force is applied to the glass sheet on the upper edge portion side, the first-direction tensile force is also applied to the lower edge portion side as a reaction force thereof. Thus, the same effect as that of the above-mentioned embodiment can be obtained. Further, in the above-mentioned second embodiment, the first-direction tensile force and the second-direction tensile force are applied to the glass sheet through use of the air cylinder. However, a hydraulic cylinder may be used instead of the air cylinder. Alternatively, the first-direction tensile force and the second-direction tensile force may be applied to the glass sheet through control using a servo mechanism.

Further, in the above-mentioned second embodiment, the chucks may be controllable independently in movement amount in the vertical direction and the horizontal direction. That is, in the first air cylinder and the second air cylinder configured to move the chucks, the air pressures inside the cylinders may be controllable independently for each chuck. With the configuration described above, the magnitude of the tensile stress to be applied between the chucks can be controlled independently.

In addition, in the above-mentioned respective embodiments, under a state in which the vertically-opposed upper and lower edge portions of the glass sheet are supported, the glass sheet is conveyed in the horizontal direction. However, under a state in which the pair of opposed edge portions of the glass sheet in the horizontal direction are supported, the glass sheet may be conveyed in the vertical direction. Further, in the above-mentioned respective embodiments, the chuck is used as the support part, but is not limited thereto. For example, a suction pad having a large number of vacuum holes for applying a negative pressure to the abutment portion (abutment surface) against each of the upper edge portion and the lower edge portion may be used.

Note that, as the glass sheet is reduced in sheet thickness and increased in area of its surface, the glass sheet is more liable to be vibrated during conveyance. Thus, the sheet member conveyance device of the present invention is suitably used for conveyance of such a glass sheet that a value of a ratio between the sheet thickness (m) and the area ($m^2$) (sheet thickness/area) is preferably $0.7 \times 10^{-3}$ or less, more preferably $0.1 \times 10^{-3}$ or less.

Example 1

As Example of the present invention, the glass sheet was conveyed in vertical orientation through use of the sheet member conveyance device having the same configuration as that of the above-mentioned first embodiment, and the amplitude of vibration occurring in the glass sheet was examined. Conditions for conducting the examination are described below.

The conveyed glass sheet was set to have dimensions of a length: 1,500 mm, a width: 2,000 mm, and a sheet thickness: 0.2 mm. Further, in the chuck groups configured to respectively support the upper edge portion and the lower edge portion of the glass sheet, the adjacent chucks were set to have a separation distance of 475 mm secured therebetween. Under such conditions, the glass sheet in a state of having the convex thread portion formed therein was conveyed. Then, the magnitude of the vibration amplitude was measured at each of the center portion and the rear end portion of the glass sheet during conveyance in the conveyance direction. The magnitude of the amplitude was measured by a laser displacement meter.

Further, as Comparative Example, the deformation support chuck of the sheet member conveyance device of Example was replaced by the flattening support chuck, and the glass sheet having the same size was conveyed in a state without the convex thread portion. Then, the magnitude of the vibration amplitude was measured at each of the center portion and the rear end portion of the glass sheet during conveyance in the conveyance direction.

Figure 9:
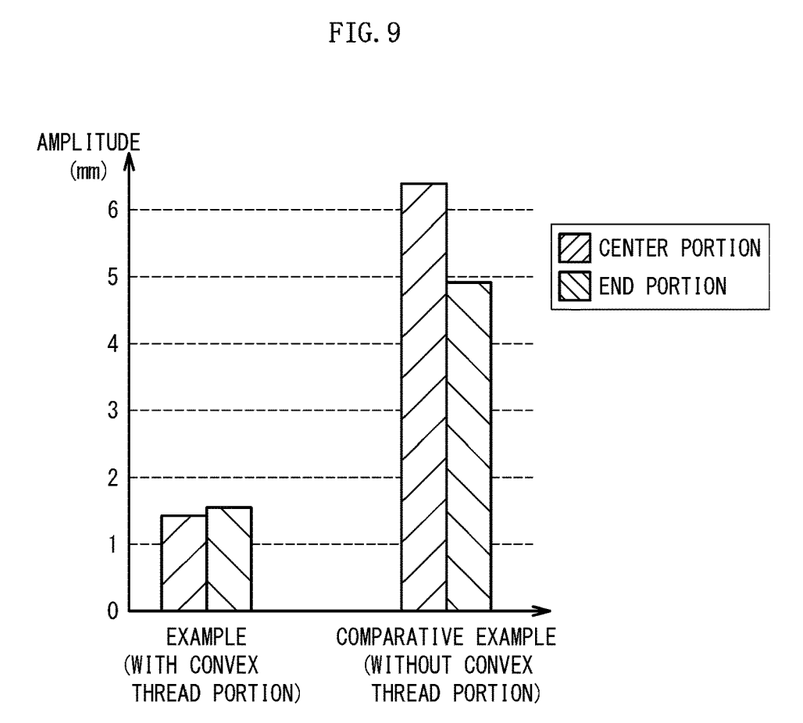
FIG. 9 is a graph for showing comparison between an amplitude of vibration occurring in the glass sheet conveyed through use of the sheet member conveyance device of the present invention and an amplitude of vibration occurring in the glass sheet conveyed through use of a device of the related art.

The results of the measurement of the magnitude of the vibration amplitude in each of Example and Comparative Example are shown in FIG. 9. As shown in FIG. 9, it is understood that the vibration amplitude at both of the center portion and the end portion in Example is smaller than that in Comparative Example. Based on the above-mentioned results, in the sheet member conveyance device of the present invention, the vibration amplitude in the entire glass sheet can be reduced when the glass sheet is conveyed in vertical orientation.

Example 2

As Example of the present invention, the glass sheet was conveyed in vertical orientation through use of the sheet member conveyance device having the same configuration as that of the above-mentioned second embodiment, and a relationship between each of the first-direction tensile force and the second-direction tensile force applied to the glass sheet during conveyance and the amplitude of vibration occurring in the glass sheet was examined. Conditions for conducting the examination are described below.

The conveyed glass sheet was set to have dimensions of a length: 1,500 mm, a width: 2,000 mm, and a sheet thickness: 0.2 mm. Further, in the chuck groups configured to respectively support the upper edge portion and the lower edge portion of the glass sheet, the adjacent chucks were set to have a separation distance of 475 mm secured therebetween. Further, the magnitude of the first-direction tensile force was set to 150 N, and the magnitude of the second-direction tensile force was set to 50 N. The glass sheet was conveyed under a state in which both of the forces are applied to the glass sheet. Further, the magnitude of the vibration amplitude was measured at each of the center portion and the rear end portion of the glass sheet during conveyance in the conveyance direction.

Further, as Comparative Example 1, through use of the same sheet member conveyance device as that of Example, the glass sheet having the same size as that of Example was conveyed under a state in which none of the first-direction tensile force and the second-direction tensile force was applied to the glass sheet (state in which the glass sheet was only supported by the chucks). Further, the magnitude of vibration amplitude was measured at each of the center portion and the rear end portion of the glass sheet during conveyance in the conveyance direction.

Further, as Comparative Example 2, through use of the same sheet member conveyance device as that of Example, the glass sheet having the same size as that of Example was conveyed under a state in which the magnitude of the first-direction tensile force was set to 150 N (constant magnitude) and only the first-direction tensile force was applied to the glass sheet. Further, the magnitude of the vibration amplitude was measured at each of the center portion and the rear end portion of the glass sheet during conveyance in the conveyance direction.

Figure 10:
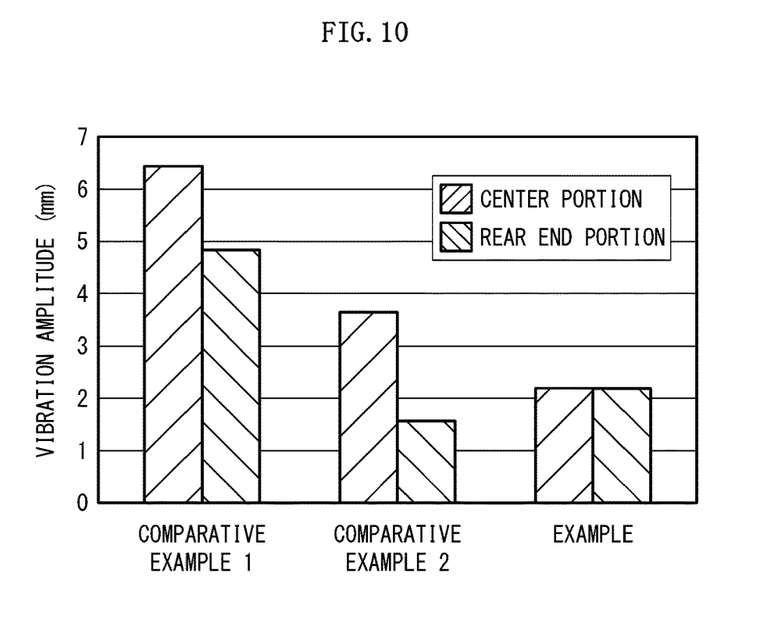
FIG. 10 is a graph for showing the amplitude of vibration occurring in the glass sheet.

The results of the measurement of the magnitude of the vibration amplitude in each of Example and Comparative Example are shown in FIG. 10. As shown in FIG. 10, it is understood that the vibration amplitude at both of the center portion and the rear end portion in the conveyance direction in Comparative Example 1 is larger than those of Example and Comparative Example 2.

Further, it is understood that the vibration amplitude at the rear end portion in the conveyance direction in Comparative Example 2 is reduced to be smaller than that in Example, whereas the vibration amplitude at the center portion is larger than that in Example. That is, in Comparative Example 2, a value of the displacement of the glass sheet in the sheet thickness direction due to the vibration is at the maximum at the center portion, and the maximum value is larger than that of Example.

In contrast to Comparative Examples, in Example, the magnitude of the vibration amplitude is substantially the same at the center portion and the rear end portion in the conveyance direction. Further, the displacement of the glass sheet in the sheet thickness direction due to the vibration is at the maximum at both of the center portion and the rear end portion in the conveyance direction, but the maximum value is smaller than those of Comparative Example 1 and Comparative Example 2.

The effect is obtained for the following reasons. That is, when the second-direction tensile force is applied under a state in which only the first-direction tensile force having a constant magnitude is applied to the glass sheet (state of Comparative Example 2), the vibration amplitude at the center portion is gradually reduced along with increase in the second-direction tensile force. Further, the vibration amplitude at the rear end portion in the conveyance direction is gradually increased along with the increase in the second-direction tensile force contrary to the center portion. As a result, the magnitude of the second-direction tensile force is adjusted so that the vibration amplitude at the center portion and the vibration amplitude at the rear end portion in the conveyance direction become substantially the same. For the above-mentioned reasons, according to the present invention, the vibration amplitude in the entire glass sheet can be reduced when the glass sheet is conveyed in vertical orientation.

REFERENCE SIGNS LIST 1 sheet member conveyance device
2 sheet member support device
3 moving mechanism
4 line sensor
5 glass sheet
6 sheet member conveyance device
7 sheet member inspection device
8, 9 chuck group
11-14 chuck pair
101, 102 deformation support chuck
111, 112 flattening support chuck
121, 122 flattening support chuck
131, 132 flattening support chuck
141, 142 flattening support chuck
31 upper frame
32 lower frame
33 upper guide rail
34 lower guide rail
41 curved convex portion
42 curved concave portion
51 upper edge portion
51a front end portion of upper edge portion in conveyance direction
51b rear end portion of upper edge portion in conveyance direction
52 lower edge portion
52a front end portion of lower edge portion in conveyance direction
52b rear end portion of lower edge portion in conveyance direction
53 convex thread portion (concave thread portion)
54 flat portion
81-85 chuck
91-95 chuck
F first-direction tensile force
P second-direction tensile force

The invention claimed is:

1. A sheet member conveyance device, comprising two support part groups each comprising a plurality of support parts arrayed away from one another along one of a pair of opposed edge portions of a sheet member in vertical orientation, the two support part groups supporting the pair of opposed edge portions of the sheet member to convey the sheet member along a longitudinal direction of the pair of opposed edge portions, wherein each of the two support part groups further comprises a first cylinder containing a first piston that moves in a direction orthogonal to the longitudinal direction of the pair of opposed edge portions to stretch, via air pressure or hydraulic pressure, the sheet member along the direction orthogonal to the longitudinal direction of the pair of opposed edge portions in a state of supporting the pair of opposed edge portions to apply a first-direction tensile force working along a direction connecting the pair of opposed edge portions between the pair of opposed edge portions of the sheet member, wherein each of the two support part groups further comprises a second cylinder containing a second piston that moves in the longitudinal direction of the pair of opposed edge portions to cause, via air pressure or hydraulic pressure, a first of the plurality of support parts in a state of supporting a first end portion of the one of the pair of opposed edge portions and a second of the plurality of support parts in a state of supporting a second end portion of the one of the pair of opposed edge portions to stretch the sheet member along the longitudinal direction of the pair of opposed edge portions to apply a second-direction tensile force working along the longitudinal direction of the pair of opposed edge portions between the first of the plurality of support parts and the second of the plurality of support parts, and wherein the first cylinder containing the first piston and the second cylinder containing the second piston of each of the two support part groups are individually adjustable to individually adjust a magnitude of the first-direction tensile force and a magnitude of the second-direction tensile force, respectively.

2. The sheet member conveyance device according to claim 1,
   wherein positions to be supported by the plurality of support parts of each of the two support part groups are symmetrical with respect to a center portion of the one of the pair of opposed edge portions, and
   wherein the plurality of support parts of a first of the two support part groups and the plurality of support parts of a second of the two support part groups are configured to support the same positions in the longitudinal direction of the pair of opposed edge portions.

3. The sheet member conveyance device according to claim 1, wherein each of the two support part groups further comprises a plurality of the second cylinders containing the second pistons to apply the second-direction tensile force between all of the plurality of support parts, which are adjacent to each other, with respect to a center portion of the one of the pair of opposed edge portions.

4. The sheet member conveyance device according to claim 1, wherein the first cylinder containing the first piston and the second cylinder containing the second piston of each of the two support part groups respectively adjust the magnitude of the first-direction tensile force and the magnitude of the second-direction tensile force applied to the sheet member by adjusting air pressure or hydraulic pressure of the respective the first cylinder containing the first piston and the second cylinder containing the second piston.

5. A sheet member inspection device, comprising a defect inspection part, which is arranged in a conveyance path of the sheet member conveyed by the sheet member conveyance device of claim 1, that inspects presence or absence of a defect contained in the sheet member.

6. The sheet member inspection device according to claim 5,
   wherein the defect inspection part scans and inspects an effective surface of the sheet member, and
   wherein the second cylinder containing the second piston of each of the two support part groups varies, depending on an inspection region of the sheet member, the magnitude of the second-direction tensile force to be applied between the plurality of support parts adjacent to each other along the one of the pair of opposed edge portions.

7. The sheet member inspection device according to claim 5, wherein the defect inspection part inspects an entire region of an effective surface of the sheet member while causing the sheet member to be conveyed.

8. The sheet member inspection device according to claim 7,
   wherein, when inspection is performed on a first region from a front end portion of the sheet member in a conveyance direction of the sheet member to a center portion of the sheet member in the conveyance direction, the second cylinder containing the second piston of each of the two support part groups increases the second-direction tensile force to be applied between the plurality of support parts adjacent to each other along the one of the pair of opposed edge portions as the first region is shifted from the front end portion in the conveyance direction to the center portion in the conveyance direction, and
   wherein, when inspection is performed on a second region from the center portion of the sheet member in the conveyance direction to a rear end portion of the sheet member in the conveyance direction, the second cylinder containing the second piston of each of the two support part groups reduces the second-direction tensile force to be applied between the plurality of support parts adjacent to each other along the one of the pair of opposed edge portions as the second region is shifted from the center portion in the conveyance direction to the rear end portion in the conveyance direction.

9. The sheet member conveyance device according to claim 1, wherein the first cylinder containing the first piston of each of the two support part groups applies the first-direction tensile force via hydraulic pressure.

10. The sheet member conveyance device according to claim 1, wherein the first cylinder containing the first piston of each of the two support part groups applies the first-direction tensile force via air pressure.

11. The sheet member conveyance device according to claim 10, wherein, in each of the two support part groups, one of the support parts is coupled to the first piston of the first cylinder to apply the first-direction tensile force.

12. The sheet member conveyance device according to claim 11, wherein, in each of the two support part groups, the second cylinder containing the second piston applies the second-direction tensile force via air pressure, the second piston of the second cylinder is coupled to the first cylinder containing the first piston, and the one of the support parts also applies the second-direction tensile force by the second air cylinder comprising the second piston.

13. A sheet member conveyance method, comprising:
   supporting a pair of opposed edge portions of a sheet member in vertical orientation by two support part groups each comprising a plurality of support parts arrayed away from one another along one of the pair of opposed edge portions;
   conveying the sheet member along a longitudinal direction of the pair of opposed edge portions;
   stretching, during the conveying of the sheet member, by a first cylinder containing a first piston, which moves in a direction orthogonal to the longitudinal direction of the pair of opposed edge portions via air pressure or hydraulic pressure, of each of the two support part groups, the sheet member along the direction orthogonal to the longitudinal direction of the pair of opposed edge portions in a state of supporting the pair of opposed edge portions to apply a first-direction tensile force working along a direction connecting the pair of opposed edge portions between the pair of opposed edge portions of the sheet member;
   stretching, by a second cylinder containing a second piston, which moves in the longitudinal direction of the pair of opposed edge portions via air pressure or hydraulic pressure, of each of the two support part groups, with a first of the plurality of support parts in a state of supporting a first end portion of the one of the pair of opposed edge portions and a second of the plurality of support parts in a state of supporting a second end portion of the one of the pair of opposed edge portions, the sheet member along the longitudinal direction of the pair of opposed edge portions to apply a second-direction tensile force working along the longitudinal direction of the pair of opposed edge portions between the first of the plurality of support parts and the second of the plurality of support parts; and
   individually adjusting the first cylinder containing the first piston and the second cylinder containing the second piston of each of the two support part groups to individually adjust a magnitude of the first-direction tensile force and a magnitude of the second-direction tensile force, respectively.

14. The sheet member conveyance method according to claim 13, wherein, in each of the two support part groups, the first-direction tensile force is applied by the first cylinder containing the first piston via hydraulic pressure.

15. The sheet member conveyance method according to claim 13, wherein, in each of the two support part groups, the first-direction tensile force is applied by the first cylinder containing the first piston via air pressure.

16. The sheet member conveyance method according to claim 15, wherein, in each of the two support part groups, one of the support parts is coupled to the first piston of the first cylinder to apply the first-direction tensile force.

17. The sheet member conveyance method according to claim 16, wherein, in each of the two support part groups, the second cylinder containing the second piston applies the second-direction tensile force via air pressure, the second piston of the second cylinder is coupled to the first cylinder containing the first piston, and the one of the support parts also applies the second-direction tensile force by the second air cylinder comprising the second piston.

* * * * *